United States Patent
Hashizume et al.

(10) Patent No.: US 8,783,121 B2
(45) Date of Patent: Jul. 22, 2014

(54) LIQUID COLLECTING SYSTEM AND A METHOD THEREFOR

(75) Inventors: Nobuya Hashizume, Kyotanabe (JP); Keishi Kitamura, Kyoto (JP); Takahiro Nishimoto, Kyoto-fu (JP); Yuichi Kimura, Chiba (JP); Chie Seki, Kamakura (JP); Iwao Kanno, Chiba (JP)

(73) Assignees: Shumadzu Corporation, Kyoto (JP); National Institute of Radiological Sciences, Chiba (JP)

( * ) Notice: Subject to any disclaimer, the term of this patent is extended or adjusted under 35 U.S.C. 154(b) by 358 days.

(21) Appl. No.: 13/256,221

(22) PCT Filed: Mar. 19, 2009

(86) PCT No.: PCT/JP2009/001244
§ 371 (c)(1),
(2), (4) Date: Sep. 12, 2011

(87) PCT Pub. No.: WO2010/106580
PCT Pub. Date: Sep. 23, 2010

(65) Prior Publication Data
US 2012/0000297 A1    Jan. 5, 2012

(51) Int. Cl.
*G01N 35/10* (2006.01)
*G01N 1/10* (2006.01)

(52) U.S. Cl.
USPC .................................... 73/864.21; 73/864.74

(58) Field of Classification Search
USPC ............... 73/864.11, 864.12, 864.73, 864.74; 356/39
See application file for complete search history.

(56) References Cited

U.S. PATENT DOCUMENTS

| | | | | |
|---|---|---|---|---|
| 3,690,833 | A | * | 9/1972 | Ferrari ............................. 436/53 |
| 5,296,378 | A | * | 3/1994 | Sakata et al. ..................... 436/63 |
| 5,399,497 | A | * | 3/1995 | Kumar et al. .................... 436/53 |

(Continued)

FOREIGN PATENT DOCUMENTS

| | | |
|---|---|---|
| EP | 0 417 305 A1 | 3/1991 |
| JP | 56-147013 A | 11/1981 |

(Continued)

OTHER PUBLICATIONS

International Search Report for the Application No. PCT/JP2009/001244 mailed Jun. 9, 2009.

(Continued)

*Primary Examiner* — Hezron E Williams
*Assistant Examiner* — Nathaniel Kolb
(74) *Attorney, Agent, or Firm* — Cheng Law Group, PLLC (57) ABSTRACT

A blood collecting apparatus includes a cleaning solution piping. The cleaning solution piping feeds into a flow path a heparin solution which is a liquid other than blood to be measured, in order to return the blood present in the flow path to a catheter disposed upstream of a blood inlet of the flow path. Thus, the blood having flowed into the flow path in an amount more than is necessary for blood collection, which corresponds to a portion returned to the upstream catheter of the blood to be measured present in the flow path, can be used in a next blood collection. As a result, the amount of collected blood can be reduced. The liquid to be measured is separated apart by means of a gas, and the flow path is cleaned in a way to leave no impurities in the flow path, thereby preventing impurities from mixing into the liquid to be measured.

21 Claims, 6 Drawing Sheets

(56) References Cited

U.S. PATENT DOCUMENTS

| | | | |
|---|---|---|---|
| 5,777,221 A * | 7/1998 | Murthy et al. | 73/149 |
| 7,218,394 B2 * | 5/2007 | Murakami et al. | 356/246 |
| 2006/0023208 A1 * | 2/2006 | Murakami et al. | 356/246 |
| 2006/0084174 A1 | 4/2006 | Ogawa et al. | |

FOREIGN PATENT DOCUMENTS

| | | | |
|---|---|---|---|
| JP | 1-307608 A | | 12/1989 |
| JP | 2-232563 A | | 9/1990 |
| JP | 2001-116666 A | * | 4/2001 |
| JP | 2001-116666 A | | 4/2001 |
| JP | 2004-109082 A | | 4/2004 |

OTHER PUBLICATIONS

Convert, L. et al., "A Microvolumetric β Blood Counter for Pharmacokinetic PET Studies in Small Animals", IEEE Transactions on Nuclear Science, 2007, vol. 54 No. 1, pp. 1-8.

Wu, Hsiao-Ming et al., "In Vivo Quantitation of Glucose Metabolism in Mice Using Small-Animal PET and a Microfluidic Device", Journal of Nuclear Medicine, 2007, vol. 48, No. 5, pp. 837-845.

Wu, HM et al., "Performing Longitudinal Measurements in Rodents Using Small Animal PET Imaging", 2008, Conf. Rec. IEEE NSS & MIC, M10-398.

Notification of Reasons for Refusal for the Application No. 2011-504614 from Japan Patent Office mailed Apr. 2, 2013.

* cited by examiner

LIQUID COLLECTING SYSTEM AND A METHOD THEREFOR

TECHNICAL FIELD

This invention relates to a liquid collecting system having a liquid collecting apparatus for collecting a liquid to be measured, as separated in a time series, and a method therefor.

BACKGROUND ART

The liquid collecting apparatus will be described taking a blood collecting apparatus which collects blood for example. The blood collecting apparatus is used for quantitative analyses in nuclear medicine diagnosis (e.g. PET (Positron Emission Tomography), SPECT (Single Photon Emission CT) and so on), and is used especially for measurement of a radioactive concentration in arterial blood of small animals (e.g. mice, rats and so on). Conventionally, the following modes (a)-(c) are employed in the quantitative analysis of the above small animals:

(a) Manual Blood Collection

Blood delivering itself under blood pressure from the other end of a catheter inserted into a mouse artery is received in a suitable receptacle. Then, a fixed volume of the blood in the receptacle is sucked up with a volumetric pipette, and a radioactive concentration in whole blood is measured by calculating (i.e. counting) radiation in the sucked-up blood. Further, plasma is obtained by centrifugal separation of the blood remaining in the receptacle, which is similarly collected with a volumetric pipette to measure a radioactive concentration in plasma.

(b) Artery Channel β-Ray Detector

A $\beta^+$ ray detector is installed in an arterial blood channel to measure a radioactive concentration in blood. $\beta^+$ rays are detected with a plastic scintillator or PIN diode. In Nonpatent Document 1, for example, a diode has a long and thin shape with a length of 30 [mm], and a detectable area is increased by installing a tube containing blood along the direction of a long side, thereby to secure detection efficiency.

(c) Microfluidic Device Mode

Figure 6:
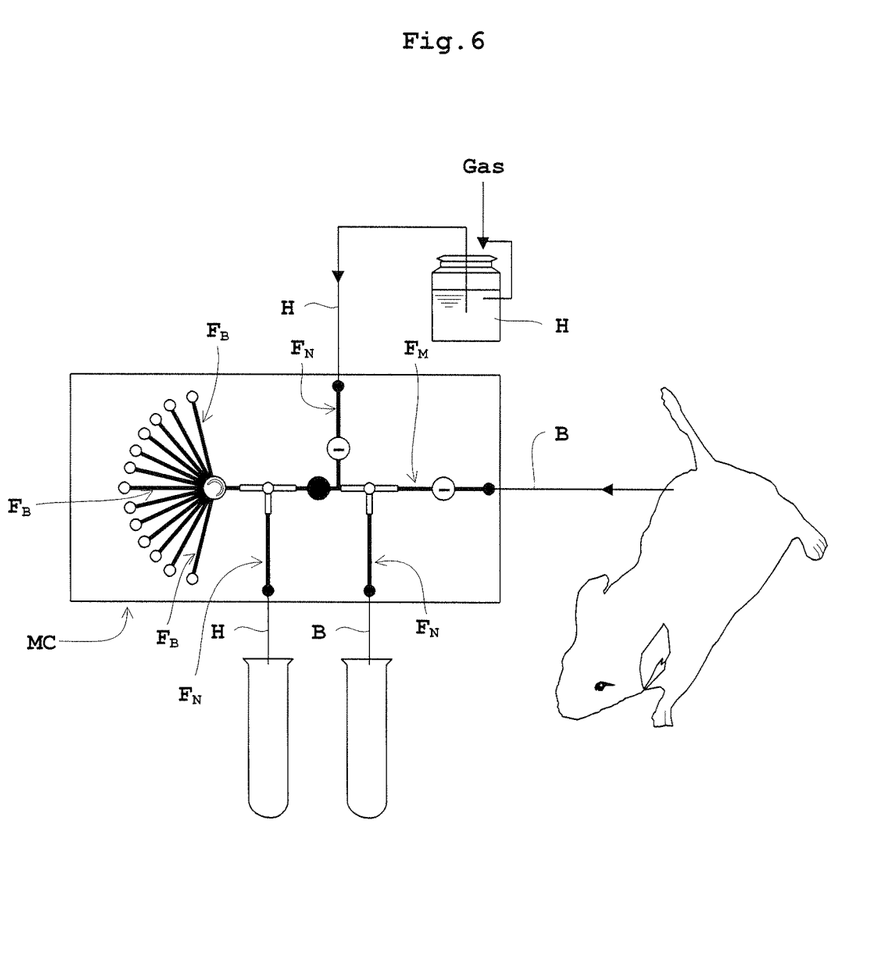
FIG. 6 is a plan view showing an entire microchip construction at the time of a conventional microfluidic device mode.

This is a mode which, as shown in FIG. 6, leads arterial blood delivering itself under mouse blood pressure onto a microchip (device) MC. The microchip MC has, arranged thereon, one main flow path $F_M$, selectable branch flow paths $F_B$, and side flow paths $F_N$ for feeding a mixed liquid H of physiological saline and heparin solution used for flow path cleaning or blood discharging, and for draining used mixed liquid H of physiological saline and heparin solution and blood B. A receptacle is placed at the end of each branch flow path $F_B$, and one of the branch flow paths $F_B$ is selected by a gas pressure of argon gas Gas supplied to the microchip MC or a mechanism of the microchip MC. With one of the branch flow paths $F_B$ selected, blood B is poured in. The flow velocity of blood B and mixed liquid H of physiological saline and heparin solution is increased by placing the interior of each branch path of the microchip MC at negative pressure, and further by providing a peristaltic pump. Each of the flow paths $F_M$ and $F_B$ is formed by grooving the microchip MC in a predetermined size. It is the characteristic of the microchip MC that a minute volume of blood B is specified if a groove length or a groove area of the poured-in blood B is known. With the blood B of a predetermined volume filling the flow paths, based on the specified minute volume, the blood B is poured along with the mixed liquid H of physiological saline and heparin solution into a predetermined receptacle (not shown) by feeding the mixed liquid H of physiological saline and heparin solution under pressure. Subsequently, each of the flow paths $F_M$ and $F_B$ is cleaned with the mixed liquid H of physiological saline and heparin solution to be ready for a next blood collection. The blood B in the receptacle is washed out along with physiological saline into another receptacle, and the radiation in the blood B is counted with a well counter (see Nonpatent Documents 2 and 3, for example).

In order to reduce the amount of collected liquid and to secure the frequency of collection, there is a liquid collecting method for collecting a liquid to be measured, as separated in a time series, by inserting a gas or a liquid other than the liquid to be measured, as separators, at designated predetermined intervals into the liquid to be measured (see Patent Documents 1 and 2, for example). As a specific technique of obtaining plasma by centrifugal separation of blood as noted hereinbefore, there is a technique of separating blood into blood cell and plasma (that is, plasma separation), for example, by centrifugal separation in a U-shaped flow path (see Patent Document 3, for example).

[Nonpatent Document 1]
L. Convert, G. M. Brassard, J. Cadorette, D. Rouleau, E. Croteau, M. Archambault, R. Fontaine, and R. Lecomte, "A microvolumetric 3 blood counter for pharmacokinetic PET studies in small animals," IEEE Nuclear Sci, vol. 54, no. 1, 2007.

[Nonpatent Document 2]
H.-M. Wu, G. Sui, C.-C. Lee, M. L. Prins, W. Ladno, H.-D. Lin, A. S. Yu, M. E. Phelps, and S.-C. Huang, "In vivo quantitation of glucose metabolism in mice using small-animal PET and a microfluidic device," J Nucl Med, vol. 48, pp. 837-845, 2007.

[Nonpatent Document 3]
H.-M. Wu, R. W. Silverman, N. G. Harris, and R. L. Sutton, "Performing Longitudinal Measurements in Rodents Using Small Animal PET Imaging", Conf Rec IEEE NSS & MIC, M10-398, 2008.

[Patent Document 1]
Unexamined Patent Publication S56-147013

[Patent Document 2]
Unexamined Patent Publication H1-307608

[Patent Document 3]
Unexamined Patent Publication No. 2004-109082

DISCLOSURE OF THE INVENTION

Problem to be Solved by the Invention

However, the modes (a)-(c) above have problems of blood collection for a designated predetermined time and an amount of collected blood. These problems will be described in detail below.

(Problem 1) Problem of Blood Collection for a Designated Predetermined Time and an Amount of Collected Blood Based on a Continuous Introduction of Blood The body weight of a mouse is assumed to be 30 [g]. Since roughly 7.5% of the body weight is blood, the total blood amount assumed is 2250 [μL]. With a loss up to about 10% of the whole blood, the influence on the physiological condition of the mouse can be disregarded, and thus a permissible maximum amount of collected blood is 225 [μL]. The blood in the connecting part of the mouse and the catheter corresponds to the starting point of blood to be collected for the designated predetermined time.

The mode (a) above is a mode in which blood is once taken out in an amount corresponding at least to the specified amount, and the specified amount is sucked up therefrom. This results in a loss of a large amount of blood. Blood collecting intervals are limited in terms of procedure, and it is difficult to collect blood for the designated predetermined time. Therefore, the sampling number (the number of blood samples) obtained within the permissible maximum amount of collected blood is small, and a quantitative analysis cannot be conducted fully.

The mode (b) above continues pouring blood into the above-noted tube at a fixed flow rate (e.g. at least 8 [µL/min] with the condition that no occlusion takes place due to blood clotting). Therefore, measurement time is restricted in order to be less than the permissible maximum amount of collected blood, and a prolonged quantitative analysis cannot be conducted.

The mode (c) above leads arterial blood of the mouse to the flow path inlet on the microchip through the catheter. When an attempt is made by this mode to collect blood for the designated predetermined time, the blood filling the catheter at the time is blood before the designated predetermined time which must be discarded. This results in a waste at every blood collecting occasion, which is considered to increase the total amount of collected blood with every blood collection.

(Problem 2) Problem of Blood Collecting Frequency

The mode (c) above once fills the blood flow paths with blood, and washes it out with the mixed liquid of physiological saline and heparin solution. Since the entire flow paths on the chip (device) are filled with blood for every blood collection, the entire flow paths need to be cleaned with the mixed liquid of physiological saline and heparin solution before moving on to a next blood collection as noted above. Therefore, blood or the heparin solution needs to be filled into the flow paths successively for every blood collection, which may consume time, and this is unsuitable to high-frequency blood collection.

(Problem 3) Problem of Impurities Mixing into Blood

The mode (c) above washes out the collected blood along with the mixed liquid of physiological saline and heparin solution into a different receptacle. It is considered that, because of the mixed liquid of physiological saline and heparin solution mixing into the blood as impurities, quantitativeness is not guaranteed.

This invention has been made having regard to the state of the art noted above, and its object is to provide a liquid collecting system and a method therefor, which can clean flow path interiors without impurities mixing into blood, and can reduce the amount of collected liquid.

Means for Solving the Problem

To fulfill the above object, this invention provides the following construction.

A liquid collecting system of this invention is a liquid collecting system having a liquid collecting apparatus for collecting a liquid to be measured, as separated in a time series, comprising (a) a flow path through which the liquid to be measured flows, (b) an extracting device provided in an intermediate position of the flow path to insert a gas or a liquid other than the liquid to be measured, as separators, at designated predetermined intervals, thereby to take out the liquid to be measured, as separated in the time series, and a dripping device for successively dripping the taken-out liquid to be measured, a liquid storage device having a plurality of grooved flow paths for storing the dripping liquid individually, and a control device for performing positional control, as interlocked to the dripping, to locate the grooved flow paths successively in a dripping position.

The liquid collecting system of this invention includes (a) a flow path and (b) an extracting device. The extracting device is provided in an intermediate position of the flow path to insert a gas or a liquid other than the above liquid to be measured, as separators, at designated predetermined intervals, thereby to take out the liquid to be measured, as separated in a time series. And the system includes a dripping device for successively dripping the taken-out liquid to be measured, a liquid storage device having a plurality of grooved flow paths for storing the dripping liquid individually, and a control device for performing positional control, as interlocked to the dripping, to locate the grooved flow paths successively in a dripping position.

The above liquid collecting system of this invention, preferably, includes (d) a gas feeding device. Specifically, the above gas feeding device feeds a gas into the flow path in order to remove the liquid to be measured or a different liquid remaining in the flow path. In the case of a gas, as distinct from a liquid, the gas itself hardly causes contamination by remaining in the flow path, and can easily remove the liquid remaining in the flow path.

Where the above gas feeding device is provided and when the above separators are the gas, the extracting device and the gas feeding device may be combined into one. That is, the extracting device uses the separators as the gas for separating into the time series and taking out the liquid to be measured. The gas feeding device feeds the gas into the flow path using the same gas and removes the liquid to be measured or the different liquid remaining in the flow path. Therefore, by combining the extracting device and the gas feeding device for use, the structures of the apparatus can be reduced by one to realize the simple apparatus.

In these liquid collecting system of this invention noted above, it is preferred that the flow path is formed by grooving planar substrates in a predetermined size. That is, with the grooving in the predetermined size, if a groove length or groove area of the liquid fed into the flow path is known, the amount of the liquid fed into the flow path can be specified based on the cross-sectional area of the groove or the depth of the groove which is grooved in the predetermined size.

One example of the grooved flow path noted above is formed of a flow path into which the liquid to be measured is fed, and a single or a plurality of flow paths for feeding the liquid other than the liquid to be measured, or the gas. By separately providing the flow path into which the liquid to be measured is fed and the flow paths for feeding the other liquid and the gas in this way, control for the liquid collection and other control (e.g. control of the gas feeding device noted above) can be carried out separately, which facilitates the control.

These liquid collecting system of this invention noted above, preferably, includes (e) an optical measuring device. Specifically, the above optical measuring device measures length information on the liquid while optically monitoring the liquid to be measured or other liquid flowing through the flow path.

A volume of the liquid to be measured which is to be taken out by the above extracting device is controlled by controlling intervals of the separators based on a result of measurement by the optical measuring device. In this way, the flow rate of the liquid, and thus the volume of the liquid, can be controlled by the intervals of the separators, and the amount of collected liquid can be minimized. The volume of the liquid to be fed can also be controlled based on the result of measurement by the optical measuring device, thereby to minimize the feed amount of the liquid.

In these liquid collecting systems of this invention noted above, one example of the liquid to be measured is blood. In this case, the liquid collecting apparatus is an apparatus for collecting blood (blood collecting apparatus). The liquid to be measured is not limited to blood, but may be a liquid including a fluorescent agent or a mixed liquid for use in an analyzing apparatus.

A liquid collecting method of this invention is a liquid collecting method for collecting a liquid to be measured, as separated in a time series, by inserting a gas or a liquid other than the liquid to be measured, as separators at designated predetermined intervals in the liquid to be measured, wherein the liquid to be measured, which is taken out as separated in a time series by insertion of the separators, is successively dripped, and positional control is performed for a liquid storage device having a plurality of grooved flow paths for storing the dripping liquid individually, such that, as interlocked to the dripping, the grooved flow paths are successively located in a dripping position.

According to the liquid collecting method of this invention, the taken-out liquid to be measured is successively dripped, and positional control is performed for the liquid storage device having a plurality of grooved flow paths for storing the dripping liquid individually, such that, as interlocked to the dripping, the grooved flow paths are successively located in the dripping position.

In the above liquid collecting method of this invention, it is preferred that, when feeding the liquid other than the liquid to be measured into the flow path, the flow path extending from the liquid inlet to a liquid outlet is filled with the other liquid. By filling up in this way, the liquid to be measured can be prevented from being fed into the flow path at a time other than collection of the liquid to be measured.

Further, when collecting the liquid to be measured, what is fed into the flow path is the liquid to be measured after the other, filling liquid is removed. With this feeding mode, continuous feeding to the flow path of the liquid to be measured is stopped, to reduce consumption of the liquid accompanying collection for the designated predetermined time, further to enable collection of the liquid to be measured for the designated predetermined time.

Further, it is preferred that, when filling the flow path extending from the liquid inlet to the liquid outlet with the liquid other than the liquid to be measured, also the portion upstream of the liquid inlet is filled with the other liquid. By filling also the upstream portion (which a catheter when blood is collected from a mouse using the catheter), the filling liquid can move the liquid to be measured in the flow path back to a location of collecting the liquid (which the connecting part of the mouse and catheter when collecting blood of the mouse using the catheter). Thus, the liquid to be measured having flowed into the flow path in an amount more than is necessary for liquid collection can be used to a maximum extent in a next liquid collection. As a result, the amount of collected liquid can be further reduced.

In these liquid collecting methods of this invention described above, it is preferred that a gas is fed into the flow path in order to remove the liquid to be measured or other liquid remaining in the flow path. In the case of a gas, as distinct from a liquid, the gas itself hardly causes contamination by remaining in the flow path, and can easily remove the liquid remaining in the flow path.

In these liquid collecting methods of this invention described above, it is preferred that, when the liquid other than the liquid to be measured remains in or fills the portion upstream of the liquid inlet, the other liquid remaining in or filling the upstream portion is fed into the flow path while collecting the liquid to be measured with the upstream portion, and the liquid inlet is closed when a boundary between the liquid to be measured and the other liquid is fed as far as the liquid inlet. When the liquid other than the liquid to be measured remains in or fills the portion (which is a catheter when blood is collected from a mouse using the catheter) upstream of the liquid inlet, the other liquid remaining in or filling the upstream portion is fed into the flow path while collecting the liquid to be measured with the upstream portion, and the liquid inlet is closed when a boundary between the liquid to be measured and the other liquid is fed as far as the liquid inlet. This allows cleaning of the other liquid in the upstream portion for a next liquid collection to be carried out simultaneously with feeding of the liquid to be measured to the liquid inlet.

In the liquid collecting system and the method therefor of this invention, it is preferable to carry out the following operation for the purpose of cleaning the inside of the flow path. That is, the flow path is filled with the liquid other than the liquid to be measured, and the flow path is cleaned by feeding gas into the flow path. In this way, the liquid other than the liquid to be measured for the predetermined time which remains in the flow path is discharged. Thus, by feeding the gas into the flow path, the liquid (residue) other than the liquid to be measured for the predetermined time which remains in the flow path is discharged promptly.

According to the liquid collecting system and the method therefor of this invention noted above, the gas is fed to discharge the liquid (residue) in the flow path other than the liquid to be measured for the predetermined time. This enables a shift to be made promptly to a next liquid collection, without leaving in the flow path the liquid other than the liquid to be measured for the designated predetermined time.

In the liquid collecting system and the method therefor of this invention, by feeding gas into the flow path to remove the remaining liquid, the liquid to be measured for the predetermined time is prevented from mixing with the other liquid. Thus, impurities (liquids other than the liquid to be measured for the predetermined time) are prevented from mixing into the liquid to be measured.

In these liquid collecting methods of this invention noted above, one example of the liquid to be measured is blood. In this case, the liquid collecting method is a method for collecting blood (blood collecting method). As noted in connection with the blood collecting apparatus, the liquid to be measured is not limited to blood, but may be a liquid including a fluorescent agent or a mixed liquid for use in an analyzing apparatus.

Effects of the Invention

According to the liquid collecting system and the method therefor of this invention, the taken-out liquid to be measured is successively dripped, and positional control is performed for the liquid storage device having a plurality of grooved flow paths for storing the dripping liquid individually, such that, as interlocked to the dripping, the grooved flow paths are successively located in the dripping position.

BRIEF DESCRIPTION OF THE DRAWINGS

FIGS. 1 (*a*) and (*b*) are outline perspective views of a blood collecting apparatus and its peripheral equipment according to an embodiment;

DESCRIPTION OF REFERENCES

10 ... blood collecting apparatus
13 ... main flow path
21 ... light source
22 ... photodiodes
41, 42, 43 ... side paths
44 ... cleaning solution piping
46 ... bubble piping

EMBODIMENT

Figure 1:
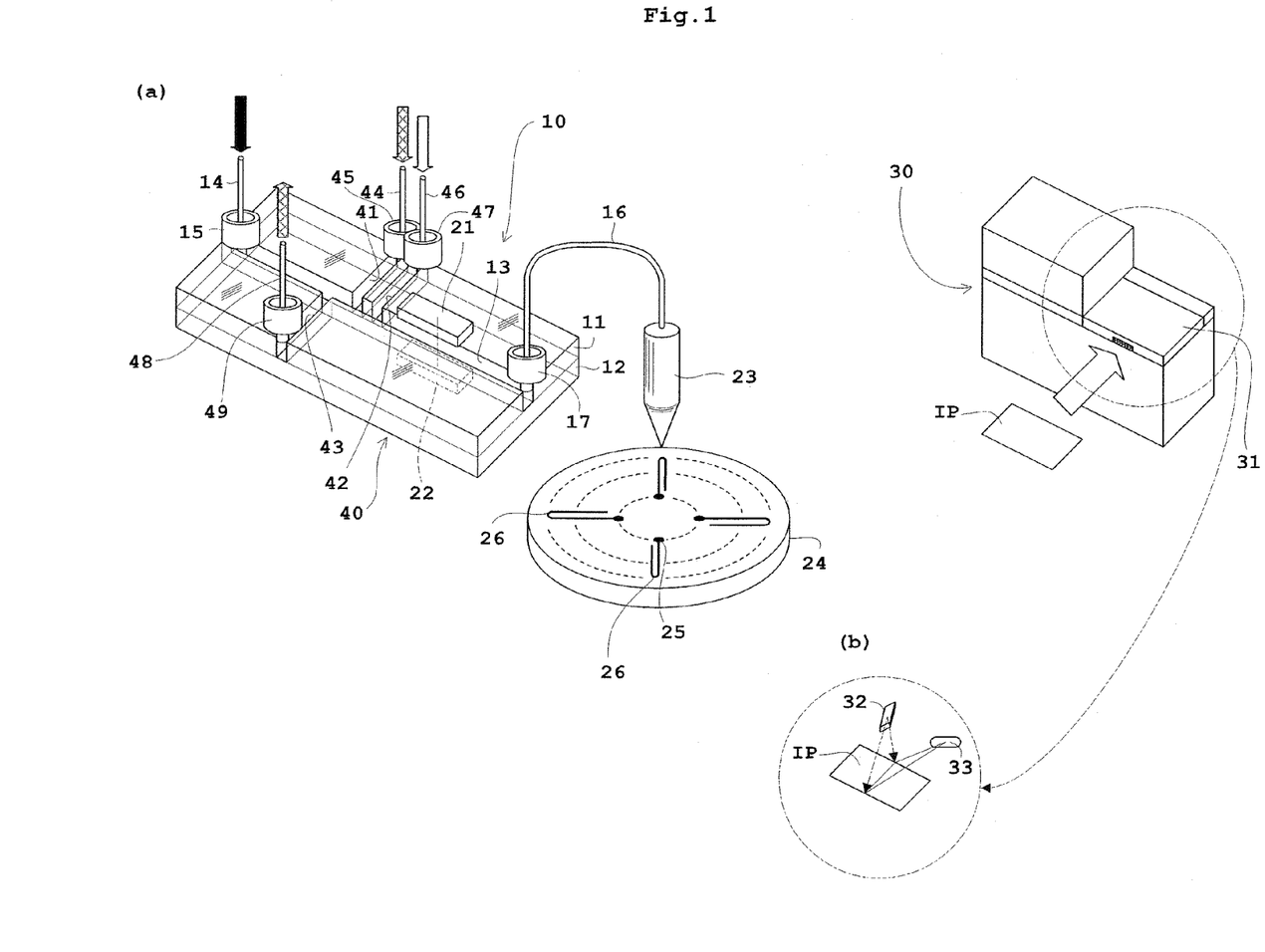
Figure 2:
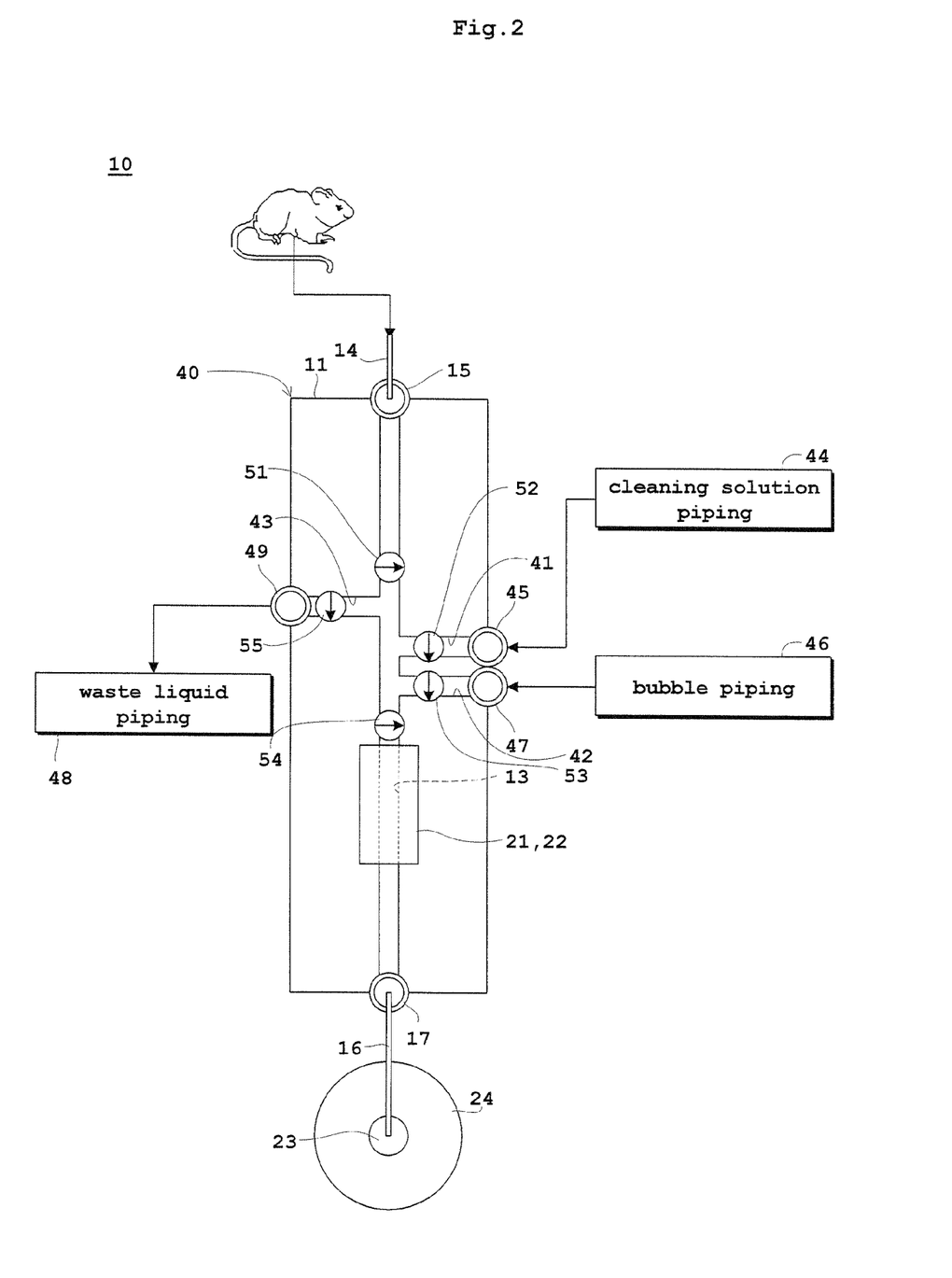
FIG. 2 is an outline plan view of a liquid dividing device of the blood collecting apparatus according to the embodiment.

An embodiment of this invention will be described hereinafter with reference to the drawings. FIG. 1 is an outline perspective view of a blood collecting apparatus and its peripheral equipment according to the embodiment. FIG. 2 is an outline plan view of a liquid dividing device of the blood collecting apparatus according to the embodiment. This embodiment will be described, taking blood as an example of liquid to be measured, and taking a blood collecting apparatus as an example of liquid collecting apparatus. Valves are omitted from FIG. 1.

As shown in FIG. 1, a blood collecting apparatus 10 according to this embodiment collects blood to be measured, as separated in a time series. Around the blood collecting apparatus 10 is a measuring apparatus 30 for measuring radiation (e.g. β-rays, γ-rays or the like) included in the blood collected by the blood collecting apparatus 10. In this embodiment, blood is collected after introducing a radioactive drug into the body of a mouse, and radiation included in the blood is measured. Further, a plasma separation is carried out, and each of the radiations included in the plasma and blood cell resulting from the plasma separation is measured. The blood collecting apparatus 10 corresponds to the liquid collecting apparatus in this invention.

The blood collecting apparatus 10 includes a liquid dividing device 40 having two PDMS substrates 11 and 12 formed of PDMS resin (Polydimethylsiloxane), one superposed on the other. The PDMS substrates 11 and 12 are grooved in a predetermined size, and grooves resulting from the grooving form a main flow path 13 and side paths 41, 42 and 43, respectively. The main flow path 13 and side paths 41, 42 and 43 correspond to the flow paths in this invention. Here, the material for the blood collecting apparatus 10 is not limited to PDMS, but may be any resin-optically transparent material such as acrylic, polycarbonate, COP (cycloolefin polymer) or the like.

A catheter 14 is disposed at a blood inlet of the main flow path 13, and the main flow path 13 and catheter 14 are connected through a connector 15. Blood is continuously fed from the catheter 14 into the main flow path 13, and its inflow volume is controlled by a valve 51 (see FIG. 2). Blood piping 16 is disposed at a blood outlet of the main flow path 13, and the main flow path 13 and blood piping 16 are connected through a connector 17. Outflow volume to a disk (also called "CD well") 24 described hereinafter is controlled by a valve 54 (see FIG. 2).

A light source 21 and photodiodes 22 are opposed to each other across the main flow path 13. Light is emitted from the light source 21 to the blood or a heparin solution, described hereinafter, flowing through the main flow path 13, and the photodiodes 22 detect light-shielding by the blood, thereby to measure length information on the blood or heparin solution described hereinafter while optically monitoring the blood or heparin solution. The light source 21 and photodiodes 22 correspond to the optical measuring device in this invention.

On the other hand, a dispenser 23 is connected downstream of the above blood piping 16. The disk 24 is disposed for receiving and storing the blood dripping from this dispenser 23. The disk 24 has a plurality of openings 25 arranged centrally and radially thereof for receiving the dripping blood. The disk 24 is grooved, as are the above PDMS substrates 11 and 12, and a plurality of U-shaped grooves 26 are formed radially by the grooving. Each U-shaped groove 26 is connected in a one-to-one relationship to one outer end of the above opening 25, and each U-shaped groove 26 is formed to extend radially of the disk 24. With the dispenser 23 interposed in this way, the disk 24 is formed capable of circulating blood with respect to the main flow path 13.

On the other hand, the measuring apparatus 30 has a reading unit 31. This reading unit 31 has a cover for inserting an exposed imaging plate IP, and detects β+ rays included in the blood by reading excited light from the imaging plate IP. Specifically, as shown in FIG. 1 (b), the reading unit 31 has a laser light source 32 and a photomultiplier tube 33. β+ rays are simultaneously detected in two dimensions by emitting laser from the laser light source 32 to the imaging plate IP, with the photomultiplier tube 33 converting to and multiplying electrons, the light excited by the laser emission to the imaging plate IP.

As noted above, and as shown in FIG. 2, the liquid dividing device 40 has the main flow path 13 for feeding blood, the side path 41 for feeding the heparin solution which is a type of anticoagulant for preventing an occurrence of blood coagulation, the side path 42 for feeding air or gas, and the side path 43 for discharging the blood or heparin solution.

Cleaning solution piping 44 is disposed at a solution inlet of the side path 41, and the side path 41 and cleaning solution piping 44 are connected through a connector 45. The flow paths are cleaned as necessary by pouring the heparin solution from the cleaning solution piping 44 through the side path 41 into the main flow path 13. Inflow volume of the heparin solution is controlled by a valve 52. The anticoagulant is not limited to the heparin solution. The cleaning solution piping 44 corresponds to the solution feeding device in this invention.

Bubble piping 46 is disposed at a gas inlet of the side path 42, and the side path 42 and bubble piping 46 are connected through a connector 47. Air or gas controlled by a pressure generator (not shown) is fed through the side path 42 into the main flow path 13, with its feed time adjusted with a valve 53. With these bubbles, blood is extracted based on length information on the blood, and waste liquids (blood, heparin solution or mixture of these) remaining in the flow paths of the liquid dividing device 40 are discharged. There is no limitation regarding the gas to be fed, but may be any gas that does not react with blood or heparin solution, which may be a rare gas such as helium, neon or argon, or nitrogen gas, for example. The bubble piping 46 corresponds to the extracting device in this invention. The bubble piping 46 corresponds also to the gas feeding device in this invention.

The bubble piping 46 feeds the gas (e.g. air) into the main flow path 13 through the side path 42, introducing the gas as bubbles at specified predetermined intervals, thereby extracting the blood to be measured, as separated in a time series. That is, the bubbles perform a function as the separators in this invention. Although a gas is used as the separators, instead of being limited to the gas, a liquid other than the liquid to be measured may be used as the separators as long as this liquid has little or no chance of mixing with the liquid to be measured (blood in this embodiment). Where the liquid to be measured is blood as in this embodiment, a liquid represented by mineral oil, fluorine-based oil or the like, which does not mix with blood, may be used as the separators. Where a gas is used as the separators, the bubble piping 46 is used both as the extracting device and as the gas feeding device. Where a liquid is used as the separators, bubble piping corresponding to the gas feeding device and separator piping corresponding to the extracting device are provided separately.

Waste liquid piping 48 is disposed at a waste liquid outlet of the side path 43, and the side path 43 and waste liquid piping 48 are connected through a connector 49. An amount of discharge is adjusted with a valve 55, to discharge, as waste liquids, part of blood other than the blood to be collected, the heparin solution after flow path cleaning, and a mixture of these.

The valve 51 is disposed downstream of the connector 15 of the main flow path 13. A valve is disposed upstream of the connector 17, light source 21 and photodiodes 22 of the main flow path 13. The valve 54 is disposed downstream of the connector 45 of the side path 41. The valve 53 is disposed downstream of the connector 47 of the side path 42. The valve 55 is disposed upstream of the connector 49 of the side path 43.

Figure 3:
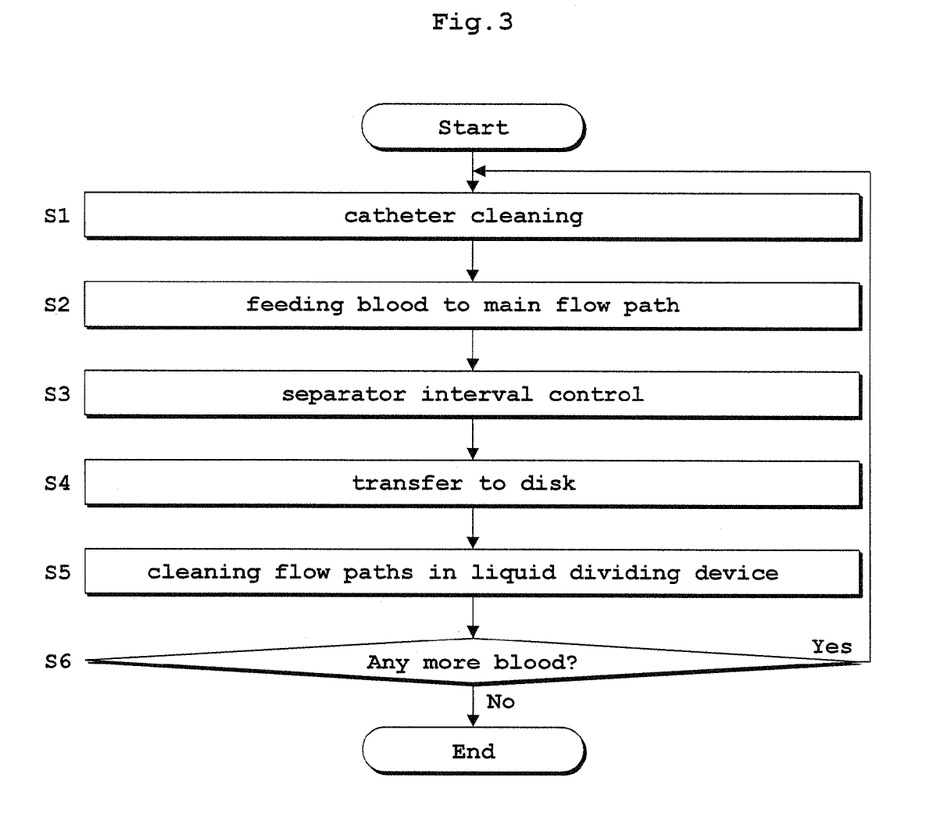
FIG. 3 is a flow chart showing a sequence of blood collecting process according to the embodiment.
Figure 4:
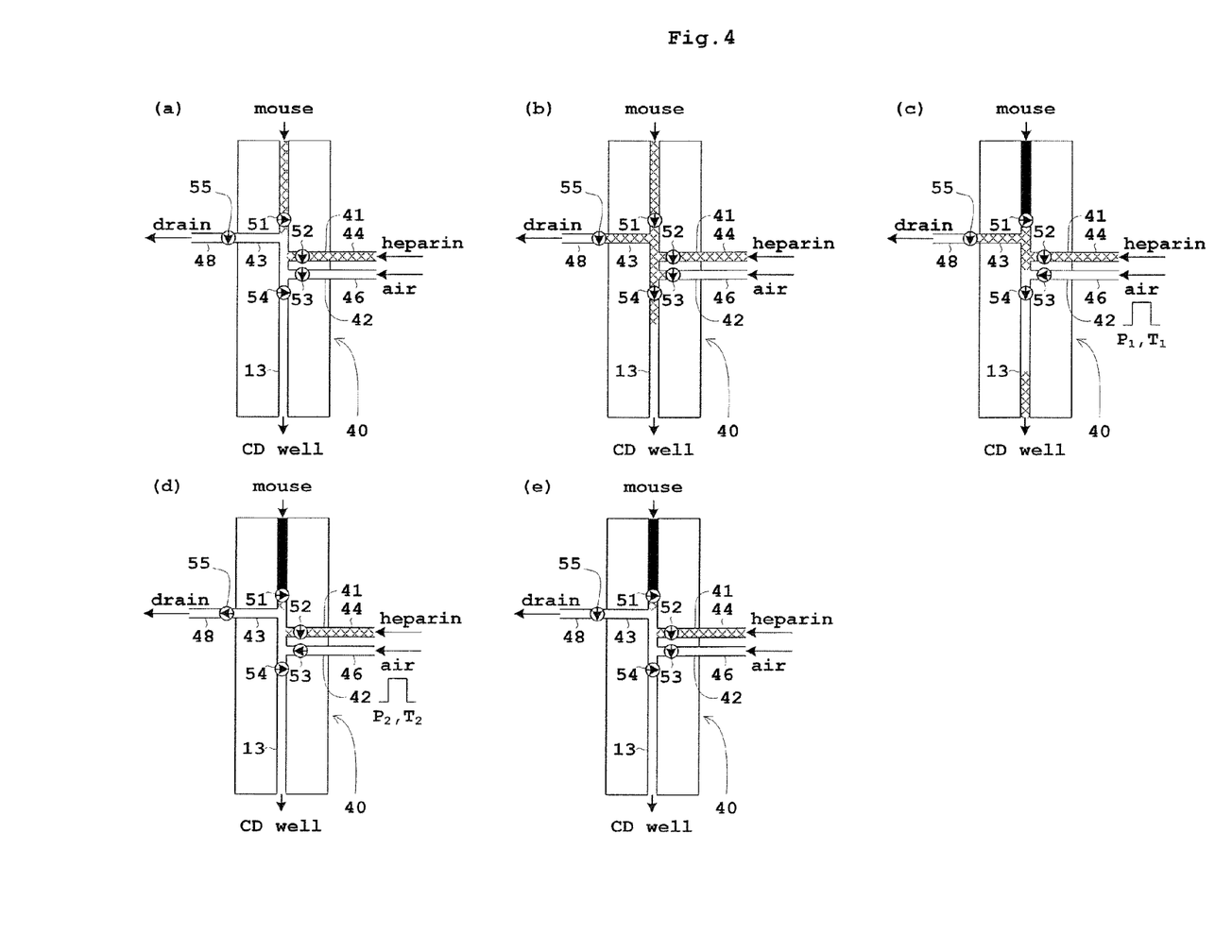
FIG. 4 is a schematic plan view of different liquids and gas showing a sequence of catheter cleaning during the blood collecting process according to the embodiment.
Figure 5:
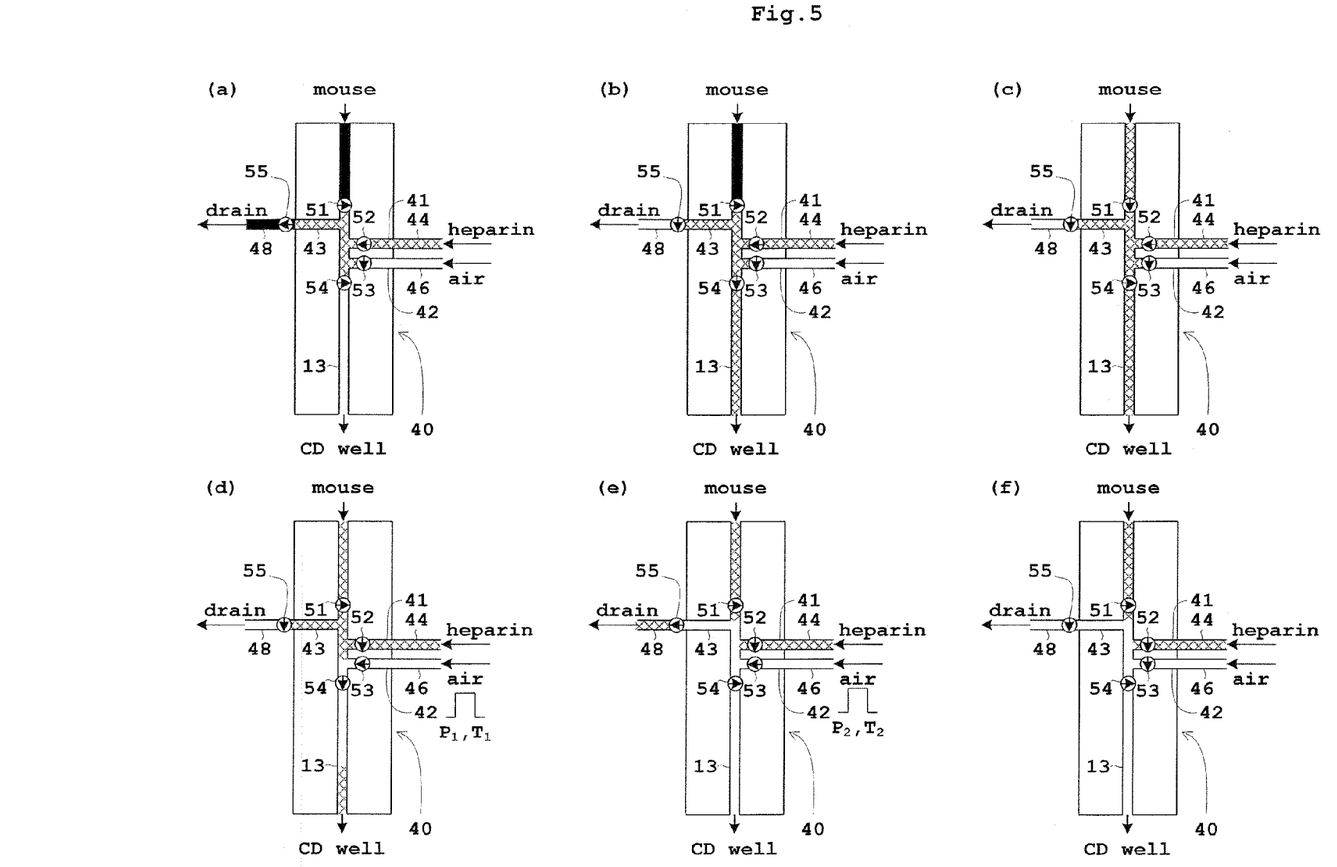
FIG. 5 is a schematic plan view of the different liquids and gas showing a sequence of cleaning flow paths in the liquid dividing device during the blood collecting process according to the embodiment.

Next, a sequence of blood collecting process will be described with reference to FIGS. 3 through 5. FIG. 3 is a flow chart showing a sequence of blood collecting process according to the embodiment. FIG. 4 is a schematic plan view of different liquids and gas showing a sequence of catheter cleaning during the blood collecting process according to the embodiment. FIG. 5 is a schematic plan view of the different liquids and gas showing a sequence of cleaning the flow paths in the liquid dividing device during the blood collecting process according to the embodiment. In FIGS. 4 and 5, illustration of the connectors, light source and photodiodes is omitted, and the valve (for waste liquids) 55 provided for the side path 43 is shown outside the liquid dividing device 40 in order to facilitate understanding of the states of the waste liquid. In FIGS. 4 and 5, the blood to be measured is shown as painted black, and the heparin solution (or a mixed liquid of heparin solution and blood) as hatched with crossed diagonal lines.

(Step S1) Catheter Cleaning

Step S1 shown in FIG. 3 is an operation for removing the heparin solution filled into the catheter 14 (see FIGS. 1 and 2) to be ready for blood collection. It is unnecessary to execute step S1 if the heparin solution is not filled into the catheter 14. This step S1 is applicable also when the heparin solution remains in the catheter 14.

First, in the liquid dividing device 40 in a standby state (see FIG. 4 (*a*)), the valves 51 and 54 are opened for the heparin solution to flow from the catheter 14 (see FIGS. 1 and 2) into the main flow path 13 (see FIG. 4 (*b*)). The flow is optically monitored by the light source 21 and photodiodes 22 (see FIGS. 1 and 2).

Specifically, when the heparin solution is not flowing through the main flow path 13, the light emitted from the light source 21 (see FIGS. 1 and 2) falls on the photodiodes 22 (see FIGS. 1 and 2) opposed to the light source 21 across the main flow path 13. Then, a detector signal having undergone a photoelectric conversion by the photodiodes 22 is outputted at High level from the photodiodes 22. Conversely, when the heparin solution is flowing through the main flow path 13, the light emitted from the light source 21 is blocked and shielded by the heparin solution. Since the light does not fall on the photodiodes 22, the detector signal is outputted at Low level from the photodiodes 22. With the photodiodes 22 detecting the light-shielding by the heparin solution, length information on the heparin solution is measured while optically monitoring the heparin solution.

The catheter 14 (see FIGS. 1 and 2) has already been inserted into a mouse artery. By inserting the catheter 14 into the mouse artery, and directing arterial blood delivering itself under mouse blood pressure to the main flow path 13 through the catheter 14, the heparin solution filling the catheter 14 is fed into the main flow path 13, while collecting blood with the catheter 14 which is a portion upstream of the blood inlet. The photodiodes 22 (see FIGS. 1 and 2) detect a boundary between the heparin solution and the blood from the mouse (indicated "mouse" in FIGS. 4 and 5) which follows the heparin solution having filled the catheter 14 and finished flowing, and then the valve 51 is closed (see FIG. 4 (*c*)). By closing this valve 51, the blood inlet will be closed when the boundary between the blood and heparin solution is fed as far as the blood inlet.

Then the valves 53 and 54 are opened to feed air (indicated "air" in FIGS. 4 and 5) or gas controlled to pressure $P_1$ by the pressure generator (not shown) from the side path 42 into the main flow path 13, which discharges (indicated "drain" in FIGS. 4 and 5) the heparin solution present in the flow paths of the liquid dividing device 40 from the blood outlet of the main flow path 13 (see FIG. 4 (*c*)). At this time, since this operation is irrelevant to the collection of blood, the blood piping 16 and dispenser 23 (see FIGS. 1 and 2 for both) may be detached by means of the connector 17 (see FIGS. 1 and 2) at the blood outlet, to prevent the heparin solution from being fed to the disk 24 (see FIGS. 1 and 2) (indicated "CD well" in FIGS. 4 and 5).

The boundary between the blood and heparin solution is indefinite. The light source 21 and photodiodes 22 (see FIGS. 1 and 2) are located downstream of the blood inlet. Since a time lag occurs after the boundary flows into the blood inlet to be detected by the photodiodes 22 until the valve 51 is closed, the blood also flows into the main flow path 13 simultaneously with the heparin solution. Therefore, when air or gas is fed from the side path 42 into the main flow path 13 to discharge the heparin solution in the flow paths of the liquid dividing device 40 from the blood outlet of the main flow path 13, besides the heparin solution, a mixed liquid of heparin solution and blood and part of the blood are also discharged as waste liquids. The optical measuring device consisting of the light source and photodiodes may be disposed adjacent the blood inlet or valve 51 to reduce the time lag after the boundary flows into the blood inlet until the valve 51 is closed. Assuming that time $T_1$ is taken for the waste liquids present from the junction of the air- or gas-feeding side path 42 and the main flow path 13 to the blood outlet to finish discharging through the blood outlet, the time $T_1$ is also taken after the valves 53 and 54 are opened until the valve 54 is closed. Therefore, air or gas will be fed from the side path 42 into the main flow path 13 for the time $T_1$ after the valves 53 and 54 are opened until the valve 54 is closed.

Since the boundary between the blood and heparin solution is indefinite, the above operation will discharge also the mixed liquid of heparin solution and blood and part of the blood as waste liquids. However, the blood adjacent the boundary between blood and heparin solution is a mixed liquid including impurities, and its discharge poses no problem.

Next, the valve 54 is closed and the valve 55 is opened to discharge a remaining part of the heparin solution (including the mixed liquid and so on) through the side path 43 and waste liquid piping 48 by means of bubbles (of air or gas) fed in under pressure $P_2$ from the side path 42 (see FIG. 4 (*d*)). Assuming that time $T_2$ is taken for the waste liquids present from the junction of the air- or gas-feeding side path 42 and the main flow path 13 to the branching point of the draining side path 43 and the main flow path 13 to finish discharging through the waste liquid piping 48, the time $T_2$ is also taken after the valve 55 is opened until the valves 53 and 55 are closed. Therefore, air or gas will be fed from the side path 42 into the main flow path 13 and waste liquid piping 48 for the time $T_2$ after the valve 55 is opened until the valves 53 and 55 are closed. The closing of the valves 53 and 55 completes the preparation for blood collection (see FIG. 4 (*e*)).

In step S1, the boundary between the blood and heparin solution fed into the main flow path 13 through the catheter 14 is optically monitored and detected at an early stage of operation. This enables blood to be collected for a designated predetermined time. That is, the blood stopped by the valve 51 shown in FIG. 4 (*e*) serves as a starting point of the blood for the designated predetermined time.

(Step S2) Feeding Blood to Main Flow Path

With the catheter 14 (see FIGS. 1 and 2) inserted into the mouse artery, arterial blood delivering itself under mouse blood pressure is fed to the main flow path 13 through the catheter 14 for the designated time. The flow of blood is controlled by opening and closing the valve 51. The control is based on the length information on the blood provided by the light source 21 and photodiodes 22 (see FIGS. 1 and 2) optically monitoring the blood.

(Step S3) Separator Interval Control

As described also in the optical measurement relating to the heparin solution, when blood is not flowing through the main flow path 13, the light emitted from the light source 21 (see FIGS. 1 and 2) falls on the photodiodes 22 (see FIGS. 1 and 2) opposed to the light source 21 across the main flow path 13. When blood is flowing through the main flow path 13, the light emitted from the light source 21 is blocked and shielded by the blood. With the photodiodes 22 detecting the light-shielding by the blood in this way, length information on the blood is measured while optically monitoring the blood. The valve 53 is controlled based on the result of measurement by the photodiodes 22. By controlling the valve 53, intervals of the air or gas fed from the side path 42 into the main flow path 13, i.e. intervals of the separators, are controlled. That is, the longer the valve 53 is opened, the longer will become the intervals of the separators, and the greater will become the gas pressure applied at one time. The shorter the valve 53 is opened, the shorter will become the intervals of the separators, and the smaller will become the gas pressure applied at one time. By controlling the intervals of the separators (i.e. bubbles in this embodiment) in this way, the force for pushing the blood in the flow paths is adjusted. Since the main flow path 13 is formed by grooving in a predetermined size, a volume of the blood to be taken out can be derived from the length information on the blood obtained from the optical monitoring.

(Step S4) Transfer to Disk

Very small amounts of blood taken out in step S3 are fed into the dispenser 23 (see FIGS. 1 and 2) through the blood piping 16 (see FIGS. 1 and 2). The feed timing and feed amounts of the very small amounts of blood are controlled by opening and closing of the valves 53 and 54 and by the pressure generator (not shown) which feeds the bubbles (of air or gas). The dispenser 23 drips each very small amount of the taken-out blood to an opening 25 (see FIG. 1) of the disk (CD well) 24 (see FIGS. 1 and 2). By this dripping, the very small amounts of the taken-out blood are transferred to the disk 24. The openings 25 and grooves 26 (see FIG. 2) are formed in the disk 24, and are used, in a number at least corresponding to the number of times of blood collection (i.e. the number of collected blood samples).

(Step S5) Cleaning Flow Paths in Liquid Dividing Device

Step S5 shown in FIG. 3 is an operation for cleaning the flow paths in the liquid dividing device 40 in order to prevent blood coagulation within the liquid dividing device 40 and catheter 14 (see FIGS. 1 and 2), and to prevent the blood at the time of collection from remaining at times other than the designated predetermined time.

First, the valve 51 is closed to stop the blood being fed from the catheter 14 (see FIGS. 1 and 2) into the main flow path 13. Then, the valves 52 and 55 are opened for the heparin solution (indicated "heparin" in FIGS. 4 and 5) to be fed through the cleaning solution piping 44 and side path 41 into the main flow path 13. The heparin solution fed into the main flow path 13 flows along with the blood remaining in the liquid dividing device 40 to the waste liquid piping 48 through the side path 43 with the valve 55 opened (see FIG. 5 (*a*)).

Next, the valve 55 is closed and the valve 54 is opened for the heparin solution fed into the main flow path 13 through side path 61 to flow toward the blood outlet of the main flow path 13 leading to the disk 24 (see FIGS. 1 and 2). This completes filling of the flow paths of the liquid dividing device 40 with the heparin solution (see FIG. 5 (*b*)). Assuming that the heparin solution is fed in an amount Hp at this time, the amount Hp is calculated from the flow path volume of the liquid dividing device 60.

Subsequently, the valve 54 is closed and the valve 51 is opened for the heparin solution fed into the main flow path 13 through the side path 61 to flow also to the catheter 14 (see FIGS. 1 and 2) to fill it up with the heparin solution (see FIG. 5 (*c*)). That is, when filling the heparin solution into the main flow path 13 extending from the blood inlet to the blood outlet, the heparin solution will fill also the catheter 14 which is upstream of the blood inlet. Assuming that the heparin solution is fed in an amount $H_C$ at this time, the amount $H_C$ is calculated from the volume of the catheter 14. By filling the heparin solution into this catheter 14, the blood present as far as the blood inlet is moved back to a blood collecting location (connecting part of the mouse and catheter 14). At this time, not only the returned blood but a quantity of the heparin solution may enter the body of the mouse, but this poses no problem.

After filling the catheter 14 (see FIGS. 1 and 2) and flow paths with the heparin solution, the valves 51 and 52 are closed and the valves 53 and 54 are opened to feed air or gas controlled by the pressure generator (not shown) to pressure $P_1$ from the side path 42 into the main flow path 13, and discharge part of the heparin solution present in the flow paths of the liquid dividing device 40 from the blood outlet of the main flow path 13 (see FIG. 5 (*d*)). As described also in step S1, the blood piping 16 and dispenser 23 (see FIGS. 1 and 2 for both) are detached by means of the connector 17 (see FIGS. 1 and 2) to prevent the heparin solution from being fed to the disk 24 (see FIGS. 1 and 2).

When the blood at the time of blood collection also remains and the heparin solution in the flow paths of the liquid dividing device 40 is discharged from the blood outlet of the main flow path 13, the mixed liquid of heparin solution and blood and also part of the blood, as well as the heparin solution, are discharged as waste liquids. In the case of pressure $P_1$ as in FIG. 4 (c) for step S1, the same time $T_1$ is taken for the waste liquids present from the junction of the air- or gas-feeding side path 42 and the main flow path 13 to the blood outlet to finish discharging through the blood outlet. Therefore, air or gas will be fed from the side path 42 into the main flow path 13 for the time $T_1$ after the valves 53 and 54 are opened until the valve 54 is closed.

Next, the valve 54 is closed and the valve 55 is opened to discharge a remaining part of the heparin solution (including the mixed liquid and so on) through the side path 43 and waste liquid piping 48 by means of the bubbles (of air or gas) flowing in under pressure $P_2$ from the side path 42 (see FIG. 5 (e)). In the case of pressure $P_2$ as in FIG. 4 (d) for step S1, the same time $T_2$ is taken for the waste liquids present from the junction of the air- or gas-feeding side path 42 and the main flow path 13 to the branching point of the draining side path 43 and the main flow path 13 to finish discharging through the waste liquid piping 48. Therefore, air or gas will be fed from the side path 42 into the main flow path 13 and waste liquid piping 48 for the time $T_2$ after the valve 55 is opened until the valves 53 and 55 are closed. The above operation leaves the flow paths of the liquid dividing device 40 in an empty state, and with the valves 53 and 55 closed, all the valves are closed to stand by until a next blood collection (see FIG. 5 (f)). Blood may be collected successively without executing step S5 where blood collecting intervals are very short, since there is no fear of blood coagulation in the flow paths, and short-time blood collecting operations can be accommodated.

(Step S6) Any More Blood?

When there is blood to be collected or when a next blood collection is carried out successively, the catheter 14 (see FIGS. 1 and 2) is filled with the heparin solution in FIG. 5 (f), which is the same state as in FIG. 4 (a), the operation returns to step S1 to be ready for blood collection, and the same process in steps S1-S6 is repeated. When there is no blood to be collected and a next blood collection is not carried out, the blood collecting sequence is ended.

After the blood collected in the blood collecting sequence is transferred to the disk 24 (see FIGS. 1 and 2), the disk 24 is rotated to carry out plasma separation for dividing into plasma and blood cell. As noted hereinbefore, the openings 25 (see FIG. 1) are open at one outer end thereof to be connected in a one-to-one relationship to the grooves 26 (see FIG. 1), thereby to carry out separation of the blood smoothly at the time of plasma separation. The grooves 26, because they are U-shaped, prevent blood cell at the time of plasma separation from escaping out of the disk 24 under centrifugal force, and cause blood cell to precipitate, after the plasma separation, at the bottom of the U-shape.

Each disk 24 (see FIGS. 1 and 2) with the plasma and blood cell having undergone the plasma separation is stored as a sample in an opened cassette not shown, the imaging plate IP (see FIG. 1) is stored thereon, and the cassette is closed. The disk 24 is taken out of the cassette after a fixed time, and the imaging plate IP is irradiated with light for exposure. Through this exposure, electrons are captured by lattice defects of a fluorescent substance (not shown) of the imaging plate IP due to the ionizing power of $\beta^+$ rays included in the blood. The exposed imaging plate IP is taken out of the cassette, and is inserted in the cover of the reading unit 31 (see FIG. 1) of the measuring apparatus 30 (see FIG. 1).

Laser is emitted from the laser light source 32 (see FIG. 1) of the reading unit 31 (see FIG. 1) to the imaging plate IP (see FIG. 1). By this irradiation, the captured electrons are excited to be conductors to recombine with holes, and are excited as light from the fluorescent substance. The photomultiplier tube 33 (see FIG. 1) converts into electrons and multiplies the light excited by the laser irradiation of this imaging plate IP, thereby simultaneously detecting in two dimensions and counting as electrical pulses. After the emission from the laser light source 32 to the imaging plate IP, the captured electrons are eliminated for reuse by emitting light from a light source for elimination (not shown) to the imaging plate IP. Based on count information on $\beta^+$ rays obtained by the imaging plate IP and reading unit 31, a radioactive concentration in the blood which is count information on $\beta^+$ rays is determined.

The blood collecting apparatus 10 and the blood collecting method therefor according to this embodiment include (a) a flow path (main flow path 13 in this embodiment), and (b) an extracting device (bubble piping 46 in this embodiment). The extracting device (bubble piping 46) is provided in an intermediate position of the flow path (main flow path 13) to insert a gas (air or gas in this embodiment) or a liquid (mineral oil, fluorine-based oil or the like when the liquid to be measured is blood) other than the above liquid to be measured (blood), as separators, at designated predetermined intervals, thereby to take out the liquid to be measured (blood in this embodiment), as separated in a time series. And (c) a liquid feeding device (cleaning solution piping 44 in this embodiment) is provided. The liquid feeding device (cleaning solution piping 44), as shown in FIG. 5 (c), feeds a liquid (heparin solution when the liquid to be measured is blood) other than the liquid to be measured (blood) into the flow path in order to return the liquid to be measured (blood) present in the flow path to a portion (catheter 14 in this embodiment) upstream of a liquid inlet (blood inlet in this embodiment) of the flow path. Thus, the liquid to be measured (blood) having flowed into the flow path in an amount more than is necessary for liquid collection (blood collection in this embodiment), which corresponds to an amount returned upstream (to the catheter 14 in this embodiment) of the liquid to be measured (blood) present in the flow path, can be used in a next liquid collection (blood collection). As a result, the amount of collected liquid (amount of collected blood) can be reduced.

In this embodiment, the blood collecting apparatus 10, preferably, includes (d) a gas feeding device (bubble piping 46 in this embodiment). Specifically, the above gas feeding device (bubble piping 46), as shown in FIGS. 4 (c), 4 (d), 5 (d) and 5 (e), feeds a gas (air, gas or the like in this embodiment) into the flow path in order to remove the liquid to be measured (blood in this embodiment) or a different liquid (heparin solution or a mixed liquid of heparin solution and blood in this embodiment) remaining in the flow path. In the case of a gas, as distinct from a liquid, the gas itself hardly causes contamination by remaining in the flow path, and can easily remove the liquid (blood, heparin solution or a mixed liquid thereof) remaining in the flow path.

In this embodiment, where the above gas feeding device is provided and when the above separators are the gas, the bubble piping 46 serves as both the extracting device and the gas feeding device. That is, in step S3, the extracting device (bubble piping 46) uses the separators as the gas (air or gas in this embodiment) for separating into the time series and taking out the liquid to be measured (blood in this embodiment). The gas feeding device (bubble piping 46) feeds the gas into the flow path using the same gas (air or gas) and, as shown in FIGS. 4 (c), 4 (d), 5 (d) and 5 (e), removes the liquid to be measured (blood) or the different liquid (heparin solution or a mixed liquid of heparin solution and blood in this embodiment) remaining in the flow path. Therefore, by using the bubble piping 46 as both the extracting device and the gas feeding device, the structures of the apparatus can be reduced by one to realize the simple apparatus.

In this embodiment, the flow paths (main flow path 13 and side paths 41, 42, and 43 in this embodiment) are formed by grooving planar substrates (PDMS substrates 11 and 12 in this embodiment) in a predetermined size. That is, with the grooving in the predetermined size, if a groove length or groove area of the liquid (blood, heparin solution or a mixed liquid thereof in this embodiment) fed into the flow paths (main flow path 13 and side paths 41, 42 and 43) is known, the amount of the liquid (blood, heparin solution or a mixed liquid thereof in this embodiment) fed into the flow paths (main flow path 13 and side paths 41, 42 and 43) can be specified based on the cross-sectional area of the grooves or the depth of the grooves which are grooved in the predetermined size.

In this embodiment, the flow paths formed by grooving are the flow path (main flow path 13 in this embodiment) into which the liquid to be measured (blood in this embodiment) is fed, and a single or a plurality of (two in this embodiment) flow paths (side path 41 for feeding the heparin solution and side path 42 for feeding air or gas in this embodiment) for feeding the liquid (heparin solution in this embodiment) other than the liquid to be measured (blood), or a gas (air or gas in this embodiment). By separately providing the flow path (main flow path 13) into which the liquid to be measured (blood) is fed and the flow paths (side paths 41 and 42) for feeding the other liquid (heparin solution) and the gas (air or gas) in this way, control for the liquid collection (blood collection in this embodiment) and other control (e.g. control of cleaning solution piping 44 corresponding to the liquid feeding device, and bubble piping 46 corresponding to the gas feeding device) can be carried out separately, which facilitates the control.

In this embodiment, the blood collecting apparatus 10, preferably, includes (e) an optical measuring device (light source 21 and photodiodes 22 in this embodiment). Specifically, the above optical measuring device (light source 21 and photodiodes 22) measures length information on the liquid (blood or heparin solution) while optically monitoring the liquid to be measured (blood in this embodiment) or other liquid (heparin solution in this embodiment) flowing through the flow path (main flow path 13 in this embodiment).

The volume of the liquid to be measured (blood in this embodiment) which is to be taken out by the above extracting device (bubble piping 46 in this embodiment) is controlled by controlling the intervals of the separators based on a result of measurement by the optical measuring device (light source 21 and photodiodes 22). In this way, the flow rate of the liquid (blood), and thus the volume of the liquid (blood), can be controlled by the intervals of the separators, and the amount of collected liquid (the amount of collected blood) can be minimized. The volume of the liquid (heparin solution) to be fed by the liquid feeding device (cleaning solution piping 44 in this embodiment) can also be controlled based on the result of measurement by the optical measuring device (light source 21 and photodiodes 22), thereby to minimize the feed amount of the liquid (heparin solution).

This embodiment describes the liquid to be measured, taking blood as an example. Therefore, the liquid collecting apparatus is an apparatus for collecting blood, i.e. the blood collecting apparatus 10. The liquid collecting method is a method for collecting blood, i.e. the blood collecting method.

In this embodiment, when feeding the liquid (heparin solution in this embodiment) other than the liquid to be measured (blood in this embodiment) into the flow path, it is preferable, as shown in FIG. 5 (*b*), to fill the flow path (main flow path 13 in this embodiment) extending from the liquid inlet (blood inlet in this embodiment) to the liquid outlet (blood outlet in this embodiment) with the above other liquid (heparin solution) (the feed amount of heparin solution being Hp). By filling up in this way, the liquid to be measured (blood) can be prevented from being fed into the flow path at a time (i.e. filling time) other than collection of the liquid to be measured (blood collection in this embodiment).

Further, when the liquid to be measured (blood in this embodiment) is collected (blood collection in this embodiment), what is fed into the flow path is the liquid to be measured (blood) after the other, filling liquid (heparin solution in this embodiment) is removed. With this feeding mode, continuous feeding to the flow path of the liquid to be measured (blood) is stopped, to reduce consumption of the liquid (blood) accompanying collection (blood collection) for the designated predetermined time, further to enable collection of the liquid to be measured (blood collection) for the designated predetermined time.

Further, when filling the flow path (main flow path 13 in this embodiment) extending from the liquid inlet (blood inlet in this embodiment) to the liquid outlet (blood outlet in this embodiment) with the liquid (heparin solution in this embodiment) other than the liquid to be measured (blood in this embodiment), it is preferable, as shown in FIG. 5 (*c*), to fill also the portion (catheter 14 in this embodiment) upstream of the liquid inlet (blood inlet in this embodiment) with the above other liquid (heparin solution) (the feed amount of heparin solution being $H_C$). By filling also the upstream portion (catheter 14), the filling liquid (heparin solution) can move the liquid to be measured (blood) in the flow path back to a location of collecting the liquid (blood) (which the connecting part of the mouse and catheter 14 when collecting blood of the mouse using the catheter 14). Thus, the liquid to be measured (blood) having flowed into the flow path in an amount more than is necessary for liquid collection (blood collection in this embodiment) can be used to a maximum extent in a next liquid collection (blood collection). As a result, the amount of collected liquid (amount of collected blood) can be further reduced.

In this embodiment, when the liquid (heparin solution in this embodiment) other than the liquid to be measured (blood in this embodiment) remains in or fills the portion (catheter 14 in this embodiment) upstream of the liquid inlet (blood inlet in this embodiment), it is preferable that, in step S1, as shown in FIG. 4 (*c*), the other liquid (heparin solution) remaining in or filling the upstream portion (catheter 14) is fed into the flow path while collecting (blood collection in this embodiment) the liquid to be measured (blood) with the upstream portion (catheter 14), and the liquid inlet (blood inlet) is closed when a boundary between the liquid to be measured (blood) and the other liquid (heparin solution) is fed as far as the liquid inlet (blood inlet). When the liquid (heparin solution) other than the liquid to be measured (blood) remains in or fills the portion (catheter 14) upstream of the liquid inlet (blood inlet), the other liquid (heparin solution) remaining in or filling the upstream portion (catheter 14) is fed into the flow path while collecting (blood collection) the liquid to be measured (blood) with the upstream portion (catheter 14), and the liquid inlet (blood inlet) is closed when a boundary between the liquid to be measured (blood) and the other liquid (heparin solution) is fed as far as the liquid inlet (blood inlet). This allows cleaning of the other liquid (heparin solution) in the upstream portion for a next liquid collection (blood collection) to be carried out simultaneously with feeding of the liquid to be measured (blood) to the liquid inlet (blood inlet).

In this embodiment, it is preferable to carry out the operation described hereinbefore for the purpose of cleaning the inside of the flow path. That is, the flow path is filled with the liquid (heparin solution in this embodiment) other than the liquid to be measured (blood in this embodiment), and the flow path is cleaned by feeding gas (air or gas) into the flow path. In this way, the liquid (heparin solution or the mixed liquid of heparin solution and blood in this embodiment) other than the liquid to be measured for the predetermined time which remains in the flow path is discharged. Thus, by feeding the gas (air or gas) into the flow path, the liquid (residue: heparin solution or the mixed liquid of heparin solution and blood in this embodiment) other than the liquid to be measured for the predetermined time which remains in the flow path is discharged promptly.

According to the liquid collecting apparatus and the method therefor in this embodiment, by feeding the gas (air or gas) to discharge the liquid in the flow path (residue: heparin solution or the mixed liquid of heparin solution and blood in this embodiment) other than the liquid to be measured for the predetermined time. This enables a shift to be made promptly to a next liquid collection (blood collection in this embodiment), without leaving in the flow path the liquid (heparin solution or the mixed liquid of heparin solution and blood) other than the liquid to be measured for the designated predetermined time.

In this embodiment, by feeding gas (air or gas in this embodiment) into the flow path to remove the remaining liquid (heparin solution or the mixed liquid of heparin solution and blood in this embodiment), the liquid to be measured (blood in this embodiment) for the predetermined time is prevented from mixing with the other liquid (heparin solution in this embodiment). Thus, impurities (liquids other than the liquid to be measured for the predetermined time) are prevented from mixing into the liquid to be measured.

This invention is not limited to the foregoing embodiment, but may be modified as follows:

(1) In the foregoing embodiment, the liquid collecting apparatus (blood collecting apparatus 10 in the embodiment) and the method therefor have been described taking blood as an example of the liquid to be measured. The liquid to be measured is not limited to blood, but may be a liquid including a fluorescent agent or a mixed liquid for use in an analyzing apparatus, for example.

(2) In the foregoing embodiment, the liquid collecting apparatus (blood collecting apparatus 10 in the embodiment) includes (d) the gas feeding device (bubble piping 46 in this embodiment). However, the gas feeding device is not absolutely necessary where there is no need to remove the liquid (blood, heparin solution or the mixed liquid thereof) remaining in the flow path, or where the liquid does not remain in the flow path. Where the separators are gas, the bubble piping 46 is used as both the extracting device and the gas feeding device. However, bubble piping for the extracting device and bubble piping for the gas feeding device may be provided separately. Where a liquid (e.g. mineral oil or fluorine-based oil) is used as the separators, bubble piping for the gas feeding device and separator piping for the extracting device may be provided separately as noted above.

(3) In the foregoing embodiment, the flow paths formed by grooving are the flow path (main flow path 13 in the embodiment) into which the liquid to be measured (blood in the embodiment) is fed, and a single or a plurality of (two in the embodiment) flow paths (side path 41 for feeding the heparin solution and side path 42 for feeding air or gas in the embodiment) for feeding a liquid (heparin solution in the embodiment) other than the liquid to be measured (blood), or a gas (air or gas in the embodiment). However, the number of feeding flow paths is not limited to two. The number of feeding flow paths is three or more where the bubble piping 46 is not used as both the extracting device and the gas feeding device as noted above. Conversely, the number of feeding flow paths may be single where the gas feeding device is not provided as noted above.

(4) In the foregoing embodiment, the liquid collecting apparatus (blood collecting apparatus 10 in the embodiment) includes (e) the optical measuring device (light source 21 and photodiodes 22 in the embodiment). However, it is not absolutely necessary to include the optical measuring device where the flow velocity is always constant. Although the light source 21 and photodiodes 22 have been described as an example of the optical measuring device, the light source 21 and photodiodes 22 are not limitative as long as the device measures the intervals of the liquid while optically monitoring the liquid to be measured. For example, a CCD camera may be employed as the optical measuring device, and volume information on the liquid to be measured may be acquired with the CCD camera. The light source 21 and photodiodes 22 are opposed to each other across the main flow path 13 as shown in FIG. 1, to constitute what is called the "transmission type sensor" for making detection based on light-shielding by the blood. Instead, what is called the "reflection type sensor" may be used to detect light reflected by the blood, with a light detecting device represented by photodiodes arranged at the same side as the light source.

(5) In the foregoing embodiment, the flow path (main flow path 13 in the embodiment) extending from the liquid inlet (blood inlet in the embodiment) to the liquid outlet (blood outlet in the embodiment) is filled with the other liquid (heparin solution) noted hereinbefore, but the filling is not absolutely necessary. With the valve 54 closed, the heparin solution may be fed into the flow path without filling the portion downstream of the valve 54, to return the blood to the catheter 14 which is the upstream portion.

(6) In the foregoing embodiment, when filling the flow path (main flow path 13 in the embodiment) extending from the liquid inlet (blood inlet in the embodiment) to the liquid outlet (blood outlet in the embodiment) with the liquid (heparin solution in the embodiment) other than the liquid to be measured (blood in the embodiment), also the portion (catheter 14 in the embodiment) upstream of the liquid inlet (blood inlet) with the above other liquid (heparin solution), but such filling is not absolutely necessary. Blood may be returned to an intermediate position of the catheter 14, instead of filling the entire catheter 14 with the blood.

The invention claimed is:

1. A liquid collecting system having a liquid collecting apparatus for collecting a liquid to be measured, as separated in a time series, comprising (a) a flow path through which the liquid to be measured flows, (b) an extracting device provided in an intermediate position of the flow path to insert a gas or a liquid other than the liquid to be measured, as separators, at designated predetermined intervals, thereby to take out the liquid to be measured, as separated in the time series, and a dripping device for successively dripping the taken-out liquid to be measured, a liquid storage device having a plurality of grooved flow paths for storing the dripping liquid individually, and a control device for performing positional control, as interlocked to the dripping, to locate the grooved flow paths successively in a dripping position;

the liquid collecting system further comprising (e) an optical measuring device for measuring length information on the liquid while optically monitoring the liquid to be measured or other liquid flowing through the flow path;

wherein a volume of the liquid to be measured which is to be taken out by the extracting device is controlled by controlling intervals of the separators based on a result of measurement by the optical measuring device.

2. The liquid collecting system according to claim 1, comprising (d) a gas feeding device for feeding a gas into the flow path in order to remove the liquid to be measured or a different liquid remaining in the flow path.

3. The liquid collecting system according to claim 2, wherein, when the separators are the gas, the extracting device and the gas feeding device are combined into one.

4. The liquid collecting system according to claim 1, wherein the flow path is formed by grooving planar substrates in a predetermined size.

5. The liquid collecting system according to claim 4, wherein the flow path is formed of a flow path into which the liquid to be measured is fed, and a single or a plurality of flow paths for feeding the liquid other than the liquid to be measured or the gas.

6. The liquid collecting system according to claim 1, wherein the liquid to be measured is blood, and the liquid collecting apparatus is an apparatus for collecting blood.

7. The liquid collecting system according to claim 1, wherein the liquid other than the liquid to be measured for a predetermined time and remaining in the flow path is discharged by filling the flow path with the liquid other than the liquid to be measured, and feeding the gas into the flow path to clean the flow path.

8. The liquid collecting system according to claim 7, wherein the liquid to be measured for the predetermined time is prevented from mixing with the other liquid, by feeding the gas into the flow path to remove the liquid remaining therein.

9. The liquid collecting system according to claim 1, wherein the liquid to be measured is a liquid including a fluorescent agent, and the liquid collecting apparatus is an apparatus for collecting the liquid.

10. A liquid collecting system having a liquid collecting apparatus for collecting a liquid to be measured, as separated in a time series, comprising (a) a flow path through which the liquid to be measured flows, (b) an extracting device provided in an intermediate position of the flow path to insert a gas or a liquid other than the liquid to be measured, as separators, at designated predetermined intervals, thereby to take out the liquid to be measured, as separated in the time series, and a dripping device for successively dripping the taken-out liquid to be measured, a liquid storage device having a plurality of grooved flow paths for storing the dripping liquid individually, and a control device for performing positional control, as interlocked to the dripping, to locate the grooved flow paths successively in a dripping position;

the liquid collecting system further comprising (e) an optical measuring device for measuring length information on the liquid while optically monitoring the liquid to be measured or other liquid flowing through the flow path; wherein a volume of the liquid to be fed is controlled based on the result of measurement by the optical measuring device.

11. A liquid collecting method for collecting a liquid to be measured, as separated in a time series, by inserting a gas or a liquid other than the liquid to be measured, as separators at designated predetermined intervals in the liquid to be measured, wherein the liquid to be measured, which is taken out as separated in a time series by insertion of the separators, is successively dripped, and positional control is performed for a liquid storage device having a plurality of grooved flow paths for storing the dripping liquid individually, such that, as interlocked to the dripping, the grooved flow paths are successively located in a dripping position;

the liquid collecting method further comprising measuring length information on the liquid with an optical measuring device while optically monitoring the liquid to be measured or other liquid flowing through the flow path; wherein a volume of the liquid to be measured which is to be taken out by the extracting device is controlled by controlling intervals of the separators based on a result of measurement by the optical measuring device.

12. The liquid collecting method according to claim 11, wherein, when feeding the liquid other than the liquid to be measured into the flow path, the flow path extending from a liquid inlet to a liquid outlet is filled with the other liquid.

13. The liquid collecting method according to claim 12, wherein, when collecting the liquid to be measured, what is fed into the flow path is the liquid to be measured after the other, filling liquid is removed.

14. The liquid collecting method according to claim 12, wherein, when filling the flow path extending from the liquid inlet to the liquid outlet with the liquid other than the liquid to be measured, also the portion upstream of the liquid inlet is filled with the other liquid.

15. The liquid collecting method according to claim 11, wherein a gas is fed into the flow path in order to remove the liquid to be measured or other liquid remaining in the flow path.

16. The liquid collecting method according to claim 11, wherein, when the liquid other than the liquid to be measured remains in or fills the portion upstream of the liquid inlet, the other liquid remaining in or filling the upstream portion is fed into the flow path while collecting the liquid to be measured with the upstream portion, and the liquid inlet is closed when a boundary between the liquid to be measured and the other liquid is fed as far as the liquid inlet.

17. The liquid collecting method according to claim 11, wherein the flow path is filled with the liquid other than the liquid to be measured, and the flow path is cleaned by feeding gas into the flow path, thereby discharging the liquid other than the liquid to be measured which remains in the flow path.

18. The liquid collecting method according to claim 17, wherein, by feeding the gas into the flow path to discharge the liquid remaining therein, the liquid to be measured for the predetermined time is prevented from mixing with the other liquid.

19. The liquid collecting method according to claim 11, wherein the liquid to be measured is blood, and the liquid collecting method is a method for collecting blood.

20. The liquid collecting method according to claim 11, wherein the liquid to be measured is a liquid including a fluorescent agent, and the liquid collecting method is a method for collecting the liquid.

21. A liquid collecting method for collecting a liquid to be measured, as separated in a time series, by inserting a gas or a liquid other than the liquid to be measured, as separators at designated predetermined intervals in the liquid to be measured, wherein the liquid to be measured, which is taken out as separated in a time series by insertion of the separators, is successively dripped, and positional control is performed for a liquid storage device having a plurality of grooved flow paths for storing the dripping liquid individually, such that, as interlocked to the dripping, the grooved flow paths are successively located in a dripping position;

the liquid collecting method further comprising measuring length information on the liquid with an optical measuring device while optically monitoring the liquid to be measured or other liquid flowing through the flow path;

wherein a volume of the liquid to be fed is controlled based on the result of measurement by the optical measuring device.

* * * * *